(12) United States Patent
Van Wieringen et al.

(10) Patent No.: US 11,235,091 B2
(45) Date of Patent: Feb. 1, 2022

(54) BREAST PUMP

(71) Applicant: KONINKLIJKE PHILIPS N.V., Eindhoven (NL)

(72) Inventors: Arjan Teodor Van Wieringen, Eindhoven (NL); Arnold Aalders, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 399 days.

(21) Appl. No.: 15/760,417

(22) PCT Filed: Sep. 16, 2016

(86) PCT No.: PCT/EP2016/072006
§ 371 (c)(1),
(2) Date: Mar. 15, 2018

(87) PCT Pub. No.: WO2017/055109
PCT Pub. Date: Apr. 6, 2017

(65) Prior Publication Data
US 2018/0250455 A1 Sep. 6, 2018

(30) Foreign Application Priority Data
Sep. 29, 2015 (EP) .................................. 15187249

(51) Int. Cl.
*A61M 1/06* (2006.01)
*F04B 11/00* (2006.01)
(Continued)

(52) U.S. Cl.
CPC .............. *A61M 1/062* (2014.02); *A61M 1/06* (2013.01); *A61M 1/75* (2021.05); *A61M 1/82* (2021.05);
(Continued)

(58) Field of Classification Search
CPC ...... A61M 1/062; A61M 1/06; A61M 1/0072; A61M 1/0031; A61M 1/0037;
(Continued)

(56) References Cited

U.S. PATENT DOCUMENTS 2,112,160 A * 3/1938 Johnson .................. A61M 5/19
604/518
2,736,332 A * 2/1956 Simmons .................. F15B 7/10
137/87.04
(Continued)

FOREIGN PATENT DOCUMENTS

| EP | 1163915 A2 | 12/2001 |
|---|---|---|
| EP | 2897666 A1 | 7/2015 |
| WO | 2015029030 A1 | 3/2015 |

*Primary Examiner* — Nathan C Zollinger

(57) ABSTRACT

There is provided a pressure oscillation damper in order to reduce the level of the pressure oscillations by the use of for a fluid extraction system. The pressure oscillation damper comprises a wall enclosing a main volume, at least two inlets, arranged in the wall and adapted to be connected to fluid extraction units, at least two outlets, arranged in the wall and adapted to be connected to pumping units, and at least one flexible member, arranged in the first volume so as to divide the first volume into at least two secondary volumes, each secondary volume forming a channel between the at least one inlet and at least one outlet, the flexible member being configured to bend toward a secondary volume having a lower pressure.

18 Claims, 7 Drawing Sheets

(51) Int. Cl.
*A61M 1/00* (2006.01)
*F16L 55/04* (2006.01)

(52) U.S. Cl.
CPC .......... *F04B 11/0016* (2013.01); *F16L 55/04* (2013.01); *A61M 2202/04* (2013.01)

(58) Field of Classification Search
CPC .............. A61M 2202/04; F04B 11/005; F04B 11/0016; F16L 55/04; F16L 27/10; F16L 55/041
USPC ..................................................... 417/423.12
See application file for complete search history.

(56) References Cited

U.S. PATENT DOCUMENTS

| | | | |
|---|---|---|---|
| 2,951,450 A | 9/1960 | Fisher | |
| 3,382,790 A * | 5/1968 | Matheson | G03D 3/06 |
| | | | 134/64 R |
| 3,720,235 A * | 3/1973 | Schrock | F16L 11/121 |
| | | | 138/137 |
| 3,804,107 A * | 4/1974 | Kozlov | A61M 1/1656 |
| | | | 137/101.31 |
| 4,263,912 A | 4/1981 | Adams | |
| 4,383,551 A * | 5/1983 | Lynch | F16L 55/052 |
| | | | 137/593 |
| 4,607,596 A | 8/1986 | Whittlestone | |
| 4,729,360 A * | 3/1988 | Fehrenbach | F02M 37/0041 |
| | | | 123/447 |
| 5,167,620 A | 12/1992 | Ureche | |
| 5,954,486 A * | 9/1999 | Iwata | F04B 43/1253 |
| | | | 417/477.3 |
| 5,954,690 A | 9/1999 | Larsson | |
| 6,039,078 A * | 3/2000 | Tamari | A61M 1/0031 |
| | | | 138/30 |
| 6,168,397 B1 * | 1/2001 | Iwata | F04B 43/0072 |
| | | | 417/477.12 |
| 6,394,142 B1 * | 5/2002 | Woelfel | F16L 11/22 |
| | | | 138/115 |
| 8,631,831 B2 * | 1/2014 | Dimalanta, Jr. | A61F 9/00736 |
| | | | 138/116 |
| 8,900,182 B2 * | 12/2014 | Britto | A61M 1/06 |
| | | | 604/74 |
| 10,100,824 B2 * | 10/2018 | Tsoukalis | A61M 5/14232 |
| 2001/0032892 A1 * | 10/2001 | Brooks | F16L 11/127 |
| | | | 239/450 |
| 2001/0038799 A1 | 11/2001 | Silver | |
| 2005/0015045 A1 | 1/2005 | Tashiro | |
| 2010/0186518 A1 | 7/2010 | Joensson | |
| 2011/0270163 A1 * | 11/2011 | Britto | A61M 1/06 |
| | | | 604/74 |
| 2013/0098456 A1 * | 4/2013 | Charlton | F04B 11/00 |
| | | | 137/1 |
| 2014/0323954 A1 | 10/2014 | Scarpaci | |

* cited by examiner

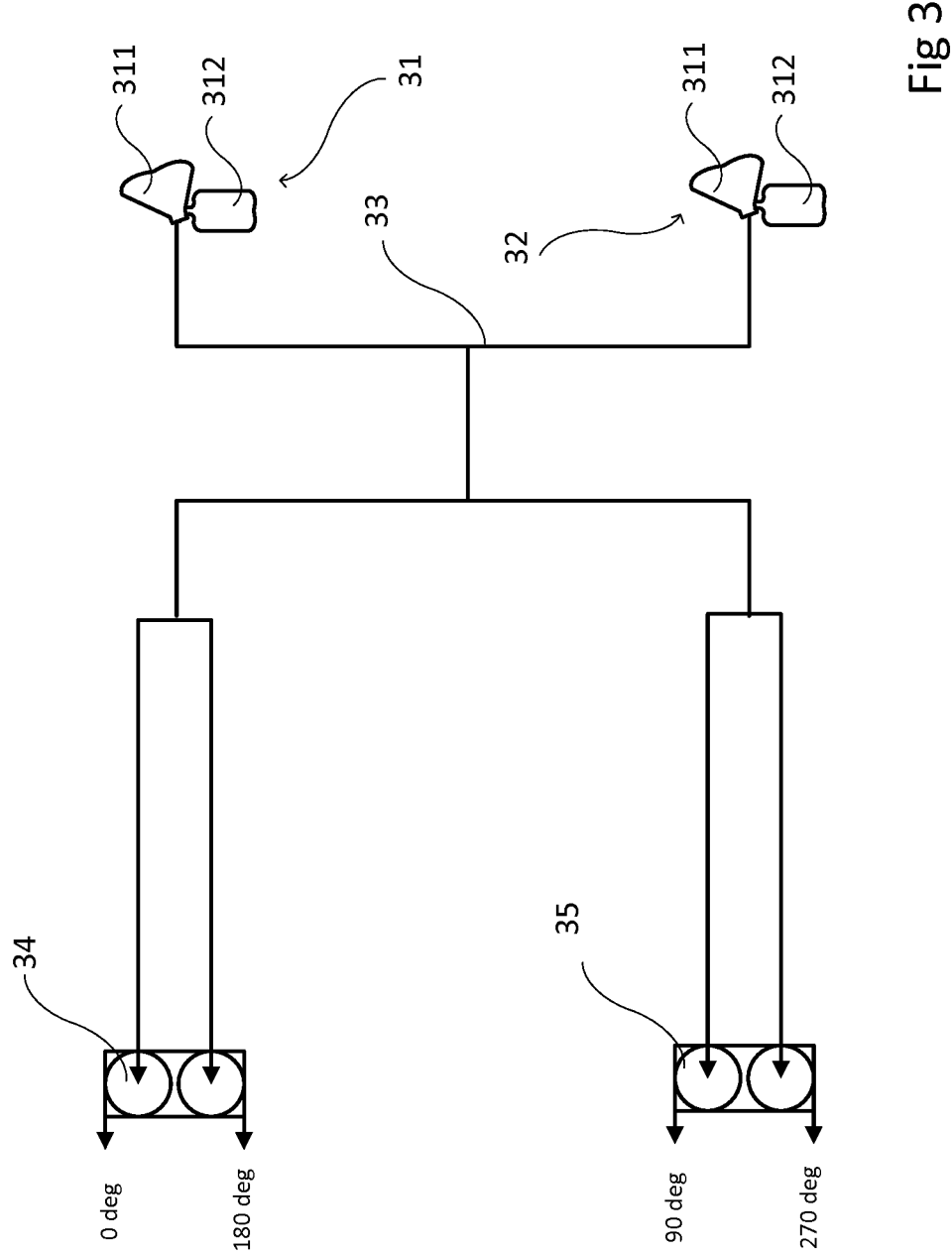

BREAST PUMP

This application is the U.S. National Phase application under 35 U.S.C. § 371 of International Application No. PCT/EP2016/072006, filed on Sep. 16, 2016, which claims the benefit of International Application No. 15187249.6 filed on Sep. 29, 2015. These applications are hereby incorporated by reference herein.

FIELD OF THE INVENTION

The invention relates pumping systems for extracting fluids, and in particular those for extracting milk from mammary glands such as women's breasts.

BACKGROUND OF THE INVENTION

Pumps used for pumping a fluid (a gas or a liquid) are often mechanical. They have a period (inlet stroke) which is when they draw the fluid into a chamber and a period (exhaust stroke) which is where the inlet is closed off and the contents of the chamber are forced out of an outlet. The total of these two periods will be called, for convenience, the pump cycle time here. Drawing the fluid in is achieved by drawing back a piston or a membrane so as to increase the volume in the chamber and forcing is out is by reversing the action so as to decrease the volume of the chamber. The displacement of the membrane or piston is also called the stroke. Changing the degree of displacement is called changing the stroke.

The pumps often used for milk expression are membrane pumps. In these the displacement of the membrane is often achieved by the reciprocating action of a moving member, for example a rotating cam.

FIG. 1 represents a curve of the change in pressure inside a volume being pumped out with such a mechanical pump. On the x-axis, time is represented while on pressure is shown on the y-axis. The dashed line 11 shows the ideal pressure change whilst the solid line 12 represents the actual pressure change over a time period. The total cycle 13 includes the inlet stroke 14 and exhaust stroke 15. During the inlet stroke 14, fluid is drawn from the volume being pumped out and so the pressure in the volume drops. During the outlet cycle, however, the inlet valve is closed and so the pressure remains constant. Therefore the pressure reduces in a series of steps rather than following the ideal straight line 11.

This step-wise pressure change, often called a pressure oscillation, is perceived as a vibration. In certain situations, such as with a breast-pump for expressing milk, the person or animal to whom the pumping is being applied may find the vibration unpleasant. Also the oscillations of the pumping may create noise which can also be undesirable.

FIG. 2 represents curves of pressure against time for a given pump pumping out different volumes and at different pump cycle times that are seen with equipment typical of a breast pump. A first curve 21 shows the pressure change when pumping out a 25 ml volume at a given speed. When the same pump is used to pump out a 50 ml volume at the same speed, a second curve 22 results which shows reduced pressure oscillation amplitude. This is equivalent to reducing the stroke for a given volume to be pumped out. Curve 23 shows the effect of increasing the pump cycle time by 20% (i.e. reducing the pumping speed by 20%) relative to the situation of curve 21. In this case, the amplitude of the oscillations is the same as for curve 21 but the duration of the oscillation is greater. Therefore it can be seen that the amplitude of the pressure oscillations is independent of the pump cycle time.

In certain cases, such as hospitals, where the apparatus is needed by many people, there is a desire to make the overall operation as fast as possible. Indeed, equipment in hospitals may be set up to pump at much higher rates than common to domestic breast pumps. Thus it is desirable that the time to the desired vacuum level ("pumping time") be as short as possible whilst still being comfortable for the user. Increasing the stroke can reduce the pumping time but this increases the pressure oscillation amplitude. Decreasing the stroke could reduce the pressure oscillation amplitude but would slow the pumping process. This could be compensated by increasing the operating frequency of the pump i.e. reducing the pump cycle time but this can impose restrictions on the choice of the pump or on its operating life-time.

There are pumps which have two chambers which are pumped alternately (called in anti-phase). For some of them, this is done be by having a single reciprocating mechanism arranged to produce an inlet stroke on one chamber while producing an exhaust stroke. Such pumps are known as two-headed pumps. Using such a pump on a single volume to be pumped can produce lower oscillations. This is by allowing the effective volume drawn into the each inlet to be smaller relative the volume being pumped out and/or giving an effective increase in the pumping speed. The same result could be achieved by using two separate pumps somehow coupled and driven in anti-phase.

SUMMARY OF THE INVENTION

Thus it is desirable to reduce the level of the pressure oscillations by providing a pressure oscillation damper for a fluid extraction system which comprises:

a wall enclosing a main volume;

At least two inlets, arranged in the wall and adapted to be connected to fluid extraction units;

At least two outlets, arranged in the wall and adapted to be connected to pumping units, and At least one flexible member, arranged in the main volume so as to divide the main volume into at least two secondary volumes, each secondary volume forming a channel between at least one inlet and at least one outlet, the flexible member being configured to bend toward a secondary volume having a lower pressure in it than is in the other secondary volume, and a restraining member to limit the bending of the flexible member The flexible member is constructed so that the pressure difference between secondary volumes and is able to cause it to bend toward the other secondary volume. This has the effect of decreasing the pressure in that secondary volume, relative to the value it would otherwise have had and increasing it in secondary volume. The effect, over a series of cycles, is to reduce or dampen the pressure oscillations. This makes the pumping system more comfortable for the person using it. Further advantages are that a wider range of pumps may be used which can allow gains in cost and size. Also, this reduces the stress on the pump and prolongs its life. This is particularly advantageous for hospitals where the equipment expected to last many times longer than in other situations.

According to an embodiment, the pressure oscillation damper has a restraining member to limit the bending of the flexible member. This avoids the flexible member bending so far as to completely close off the channel into which it is bending. Such closing off of that channel stops that channel being pumped out which, in turn, reduces the efficiency of the pumping. It could be possible to alleviate this problem by closing off the other unused channel but this has the disadvantages of requiring user intervention and perhaps training. It may also lead to errors.

Therefore the restraining member gives the advantage that the apparatus can be used with a single milk expression unit while not requiring the intervention of someone to close off of the other channel. This gives greater convenience for the users as a whole in that the apparatus can be used more quickly, with less need for training and with fewer errors.

According to an embodiment, the pressure oscillation damper has the restraining member as a protuberance attached to the wall and arranged to project into the volume. This has the advantage that the restraining member can be formed at the same time as the outer wall, simplifying the manufacturing process.

According to an embodiment, the pressure oscillation damper has the secondary volumes being defined by the walls of a flexible tube and the flexible tubes are arranged in proximity within an outer non-flexible wall.

This arrangement has the advantage that the inside of the tubes and the secondary volumes be in one piece and there would be no discontinuities. Since discontinuities can give rise to hygiene issues, they require more rigorous cleaning so limiting their number is desirable. Here the pressure oscillation damper is completed by putting the tube together and clamping the outer wall around them at the appropriate point, as opposed to attaching a number of tubes to connectors.

According to an embodiment, the pressure oscillation damper has the flexible tubes having thinner walls in a length portion arranged which is enclosed within the non-flexible wall and has thicker walls outside the length portion. The flexible tubes are also arranged to be connectable to another apparatus.

Simply varying the thickness of the tube allows the manufacturing of the tube be simplified. Making the other ends of the tubes connectable makes them easier to use.

According to an embodiment, the pressure oscillation damper has as the restraining member, a plurality of protuberances arranged longitudinally on the inside of the wall of the flexible tube.

This arrangement further helps with the hygiene requirements in making it easier to clean the insides of the tubes and may make the molding of the tubes simpler.

According to an embodiment, the flexible member is made of silicone rubber. This material has the advantage of meeting certain hygiene requirements and being easy to mold.

According to an embodiment, the flexible member is at least partially made from one of PP foil, PE foil, PUR foil, polyester, Nylon, PVC, natural rubber, PET, acetate film, polyimide, PTFE or PEEK film and the outer wall is at least partially made from one of polycarbonate, PETStyrene or ABS.

For certain situations, one or more of these may offer advantages of price or ease-of-manufacture.

According to an embodiment the fluid extraction system is a breast pump. This is an advantageous use because the stringent requirements of comfort, hygiene, speed and ease-of-use are addressed by an embodiment.

In another aspect, there is provided a fluid pumping system which comprises:

A pump having at least one inlet and at least one outlet, and

A pressure oscillation damper of any preceding claim.

Thus the basis for system which has reduced pressure oscillations amplitude compared to the same system without the pressure oscillation damper is provided. This system may then be coupled to fluid extraction units such as milk expression systems.

According to an embodiment, the fluid pumping system has a two-headed pump. Such pumps are more compact.

According to an embodiment, the fluid pumping system has both heads of the pump coupled to the same outlet of the pressure oscillation damper. This further reduces the pressure oscillations amplitude.

According to an embodiment, the fluid pumping system has the pressure oscillation damper coupled to the at least one inlet of the pump. This arrangement reduces the pressure oscillations transmitted to the user.

According to an embodiment, the fluid pumping system has the pressure oscillation damper coupled to the at least one outlet of the pump. This arrangement reduces the noise generated by the pressure oscillations.

In another aspect, there is provided a method of damping pressure oscillations for a fluid extraction system which comprises;

Providing a first volume between an inlet and an outlet so as to form a channel between inlet and outlet;

Providing a second volume between an inlet and an outlet, so as to form a channel between inlet and outlet;

Arranging a flexible member between the first and second volumes;

Pumping the first volume with a different phase relative to the second volume so that the flexible member bends toward the volume having the lower pressure, and limiting the bending of the flexible member so as to prevent the flexible member bending so far as to block the channel.

According to an embodiment, the method has the pumping being performed using more than two phases.

BRIEF DESCRIPTION OF THE DRAWINGS

FIG. 3 represents a system for milk extraction where two expression units are coupled to two two-headed pumps.

DETAILED DESCRIPTION OF THE EMBODIMENTS

Figure 1:
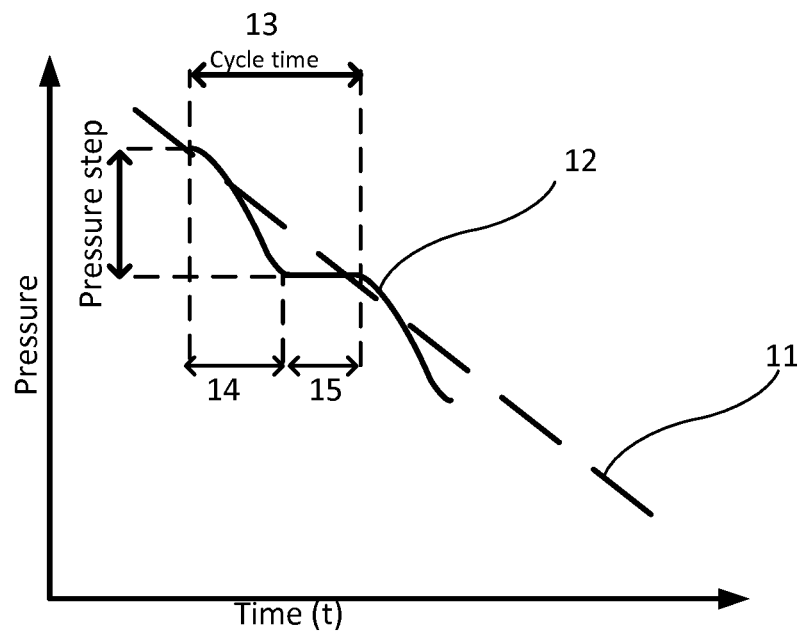
FIG. 1 represents a curve of pressure over time inside a volume being pumped out by a typical mechanical pump.
Figure 2:
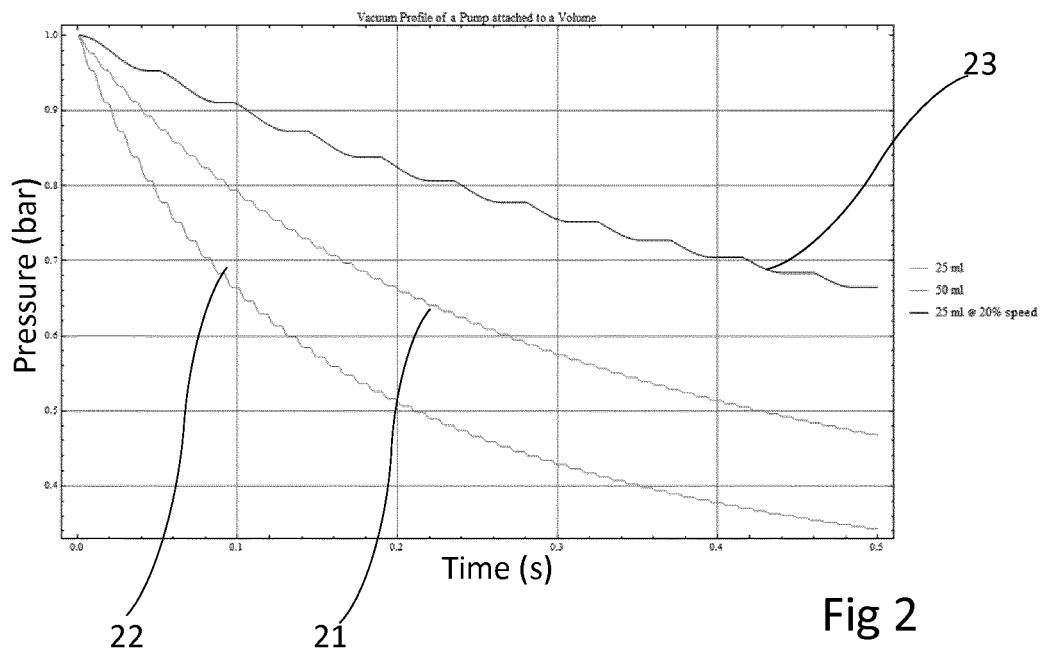
FIG. 2 represents a comparison of three curves of pressure over time.

In the following description, like references designate like elements. Furthermore, in the interests of brevity, features will only be described once except and where appropriate. The embodiments described herein are given purely as examples and without limitation. The reference signs are purely for illustration and are not limiting wherever used, including in the claims.

FIG. 3 represents a possible way of reducing the amplitude of pressure oscillations whilst still achieving an acceptably quick overall pumping operation. Two fluid extraction units such as milk expression units 31, 32 are connected by a network of tubes 33 to a pair of two-headed pumps 34, 35 such that each milk expression unit 31, 32 is connected to both of the two-headed pumps 34, 35. Each of the milk expression units has a cup 311 which is applied to the breast and, preferably, a container 312 for receiving the milk. The pair of two-headed pumps are controlled such that their phases are offset by 90°. This means that each milk expression units sees four inlet strokes in the same time compared to the case where it was attached to a single pump. This does reduce the pressure oscillation amplitude. However the system has the drawback that both milk expression units 31, 32 must be used. If it is desired to use only one milk expression units 31, 32, then the other must be closed off. Closing of can be achieved, for example, by placing a stopper in the hole (not shown) in the cup 311 through which the milk is drawn or in the end of the tube 33 which connects to the unused milk expression unit 31, 32. Failing to do this means that the pump inlets are open directly to atmospheric pressure and cannot effectively pump out the expression unit 31, 32 which is in use. The consequence of this requirement is that this system requires more training and vigilance to avoid errors and waste.

Figure 4A:
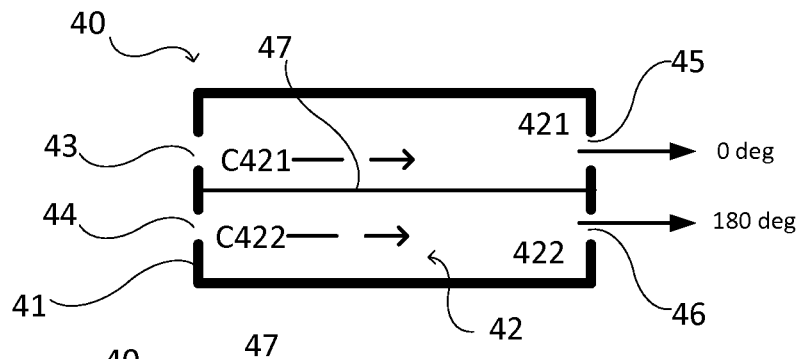
FIG. 4 represents a pressure oscillation damper according to an embodiment.

FIG. 4a represents an example of an embodiment of a pressure oscillation damper 40 which provides a way of reducing the amplitude of the pressure oscillations. An outer wall 41 defines a chamber or main volume 42. Through the wall passes a pair of inlets 43, 44 and a pair of outlets 45, 46. In the main volume 42, there is a flexible member 47 (for example a membrane or a diaphragm) which is arranged to divide the main volume 42 into two secondary volumes (or chambers) 421, 422. Each of the secondary volumes 421, 422 has an inlet 43 or 44 and an outlet 45 or 46 such that the secondary volume 421, 422 forms a channel, or passage, C421, C422 between inlet and outlet.

Figure 4B:
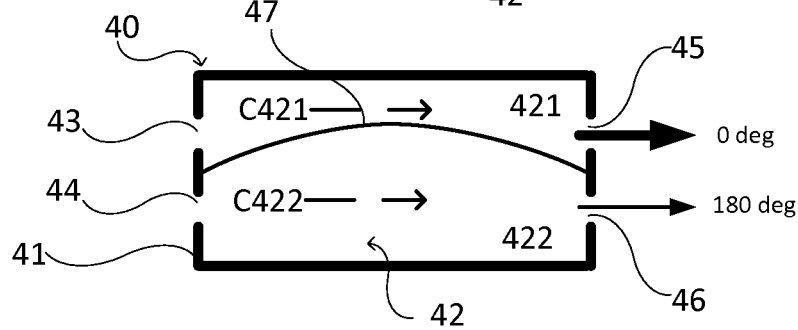
Figure 4C:
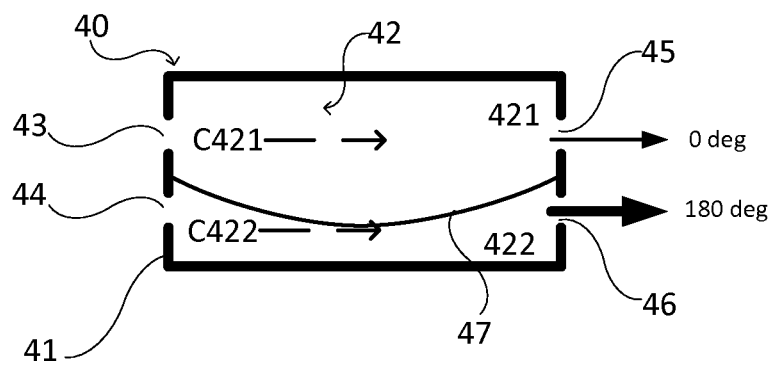

FIGS. 4b and 4c represent the action of the pressure oscillation damper.

In FIG. 4b, where the 0° phase is being pumped (the pump or pump-head coupled to it is on its inlet stroke), secondary volume 421 is at a lower pressure than is secondary volume 422. The pressure difference exerts a force on the flexible member 47. The flexible member 47 is constructed so that the pressure difference between secondary volumes 421 and 422 is able to cause it to bend toward secondary volume 421. This has the effect of decreasing the pressure in secondary volume 422, relative to the value it would otherwise have had and increasing it in secondary volume 421, in accordance with Boyle's law.

In FIG. 4c, the 180° phase is being pumped and so the flexible member 47 bends in the opposite direction, increasing the pressure in volume 422 and reducing in secondary volume 421.

Over a series of cycles, the effect of this is to reduce or dampen the pressure oscillations. Where this is being used with a breast pump, this can make use of the breast pump more comfortable for the woman using it. Further advantages are that a wider range of pumps may be used which can allow gains in cost and size. Also, this reduces the stress on the pump and prolongs its life. This is particularly advantageous for hospitals where the equipment expected to last many times longer than a domestic breast pump.

In the case of a breast pump for women, a possible choice for the flexible member 47 is a membrane or diaphragm of silicone rubber. This has the advantage of meeting the hygiene requirements and being easy to mold. Such a material can be made flexible by selecting the thickness and the exact composition. In other situations, other choices may be preferred.

The outer wall 41 is preferably made so that it does not undergo significant deformation under the pumping action. The more the outer wall 41 bends, the more the expansion of the secondary volume 421, 422 not undergoing the inlet stroke of its pump will be to the exterior. This will in turn reduce the bending of the flexible member 47 and so reduce the effectiveness of the pressure oscillation damper 40.

Figure 5:
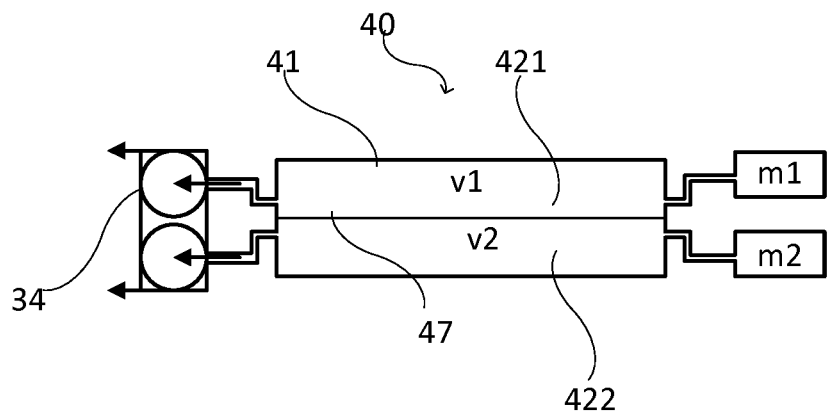
FIG. 5 represents a model of a system for milk extraction for illustrative purposes.
Figure 6:
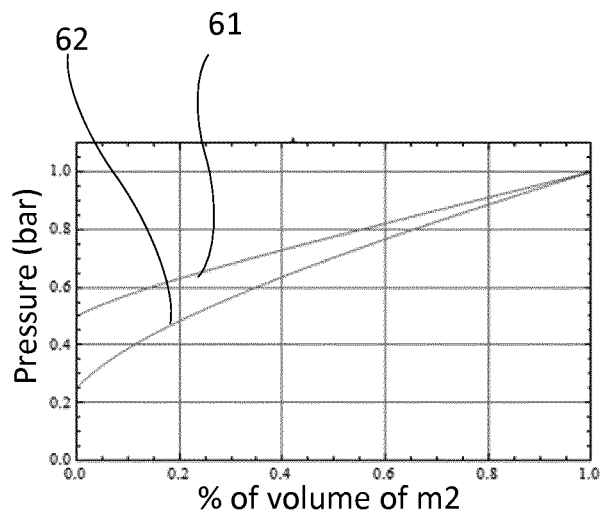
FIG. 6 represents a simulation of pumping out one of the volumes in FIG. 5.

FIGS. 5 to 7 illustrate a simulation of an ideal case and the results which show the effects of the embodiment.

FIG. 5 represents the model used to produce the illustrative results below. A two-headed pump 34 is arranged to apply 0° and 180° phase pumping, one head being coupled to a first channel C421 of a pressure oscillation damper 40 according to an embodiment and the other head being coupled to a second channel C422. The first channel C421 is coupled to a volume m1 and the second channel C422 is coupled to a volume m2, equal in volume to m1.

FIG. 6 represents a simulation of the pressure in each of the volumes m1 and m2 when volume m2 is pumped out. Curve 61 shows the pressure in volume m1 and curve 62 that in volume m2. The pressure in volume m2 reduces as a result of the pumping according to curve 62. Even though volume m1 is not being pumped out, as curve 61 shows, the pressure there also reduces. This result of the bending action of the flexible member 47. The degree to which this happens can be affected by the stiffness of the flexible member 47.

Figure 7A:
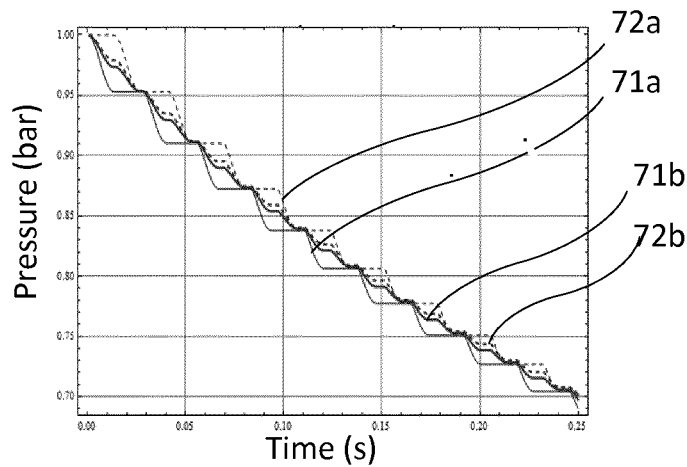
FIGS. 7a and b represent a simulations comparing pumping the volumes in FIG. 5 with and without a pressure oscillation damper according to an embodiment.

FIG. 7a represents a simulation of the change of pressure over time when both volumes m1 and m2 are each pumped out each by one head of a pump (or a single-headed pump), with and without the use of a pressure oscillation damper according to an embodiment. Curves 71a and 72a show the pressure changes in volumes m1 and m2 respectively without the use of the pressure oscillation damper. The pressure changes in volumes m1 and m2 are 180° out of phase and a significant pressure oscillation can be seen in the large steps exhibited by both curves. Curves 71b and 72b show the pressure changes in volumes m1 and m2 respectively with the use of the pressure oscillation damper according to an embodiment. Two things may be observed from curves 71b and 72b. Firstly it can be seen clearly that the ripples on the curves are much smaller meaning that the pressure oscillations are reduced. Secondly it can be seen that though the ripples are much reduces in amplitude, they occur twice as often because a pressure drop in one side cause a pressure drop in the other so both sides effectively 'see' twice the number of inlet cycles.

Figure 7B:
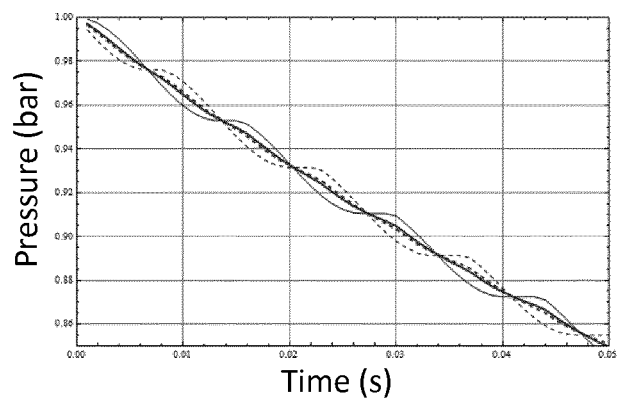

FIG. 7b represents a simulation of the pressure changes over time when each volume is pumped out using a two-headed pump. The heads of each pump are 180° out of phase and the two pumps are offset in phase by 90°. It can be seen by comparison with FIG. 7a that a further significant reduction in the pressure oscillation amplitude has been obtained. The outer curves are without a pressure oscillation damper and the inner ones (closer to the ideal line) are with a pressure oscillation damper according to an embodiment.

Figure 8:
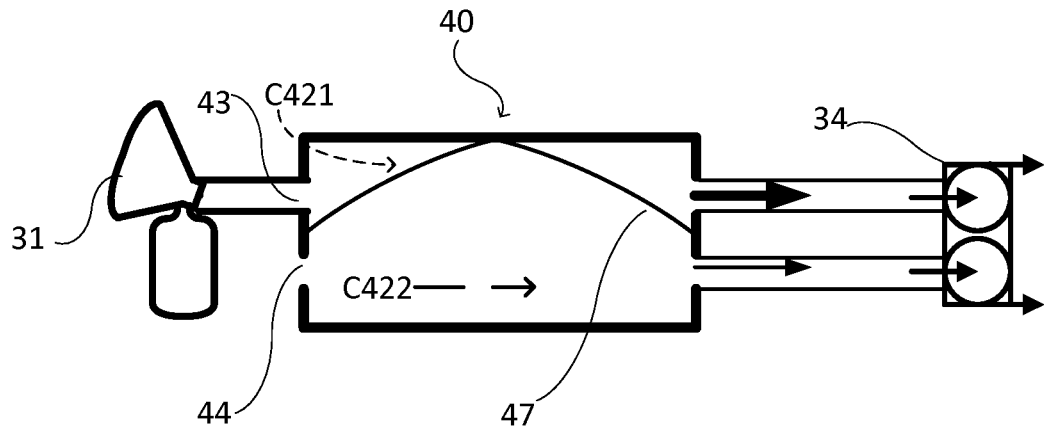
FIG. 8 represents an embodiment in a situation where a channel has been closed off under the action of the pumping.

FIG. 8 represents the situation where only one channel is connected to a fluid extraction unit. Here a milk expression unit 31, in this example, is being used on the first channel C421. Though both channels C421, C422 are being pumped by a two-headed pump 34, the other channel C422 is permanently open to atmospheric pressure via inlet 44. Here the pressure difference between the secondary volumes 421 and 422 is large enough to bend the flexible member 47 so far that it contacts the outer wall 41. This blocks that channel so that the milk expression unit 31 is no longer under suction, thereby making the pumping significantly less effective. It could be possible to alleviate this problem by closing off the other unused channel but this has the disadvantages of requiring user intervention and perhaps training. It may also lead to errors.

Figure 9:
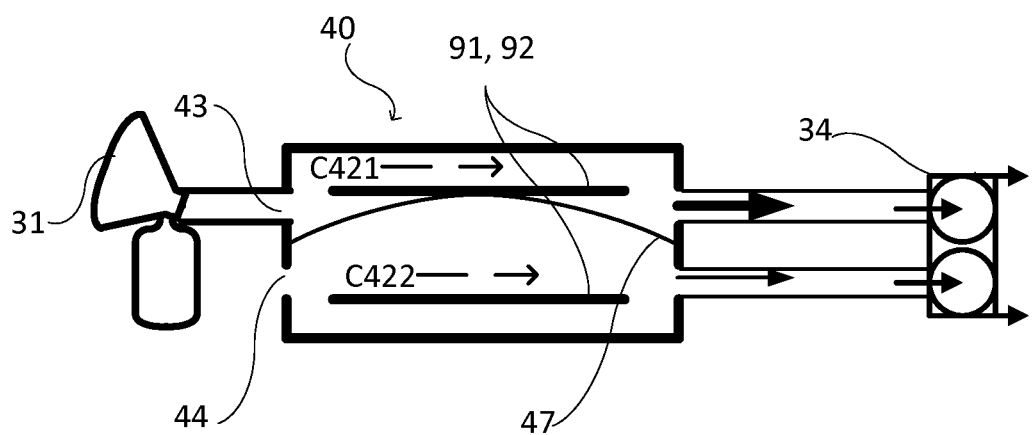
FIG. 9 represents an embodiment adapted to deal with the situation of FIG. 8.

FIG. 9 represents an example of an embodiment 90 which seeks to address the problem of blocking of a channel. In addition to the features already described, inside each secondary volume 421, 422 is placed a restraining member 91, 92. These restraining members 91, 92 are attached to the outer wall 41. The restraining members 91, 92, like the outer wall 41, work better when not susceptible to bending under the pressures that are applied in the situation in which is intended for use. The restraining members 91, 92 are arranged so as to prevent the flexible member 47 bending so far as to block the channel C421, C422.

This has the advantage that the apparatus can be used with a single milk expression unit while not requiring the intervention of someone to close off of the other channel. This gives greater convenience for the users as a whole in that the apparatus can used more quickly, with less need for training and with fewer errors.

The restraining member 91, 92 may be formed as a protuberance projecting from the outer wall 41 into the enclosed main volume 42. This has the advantage that it can be formed at the same time as the outer wall, simplifying the manufacturing process.

Figure 10A:
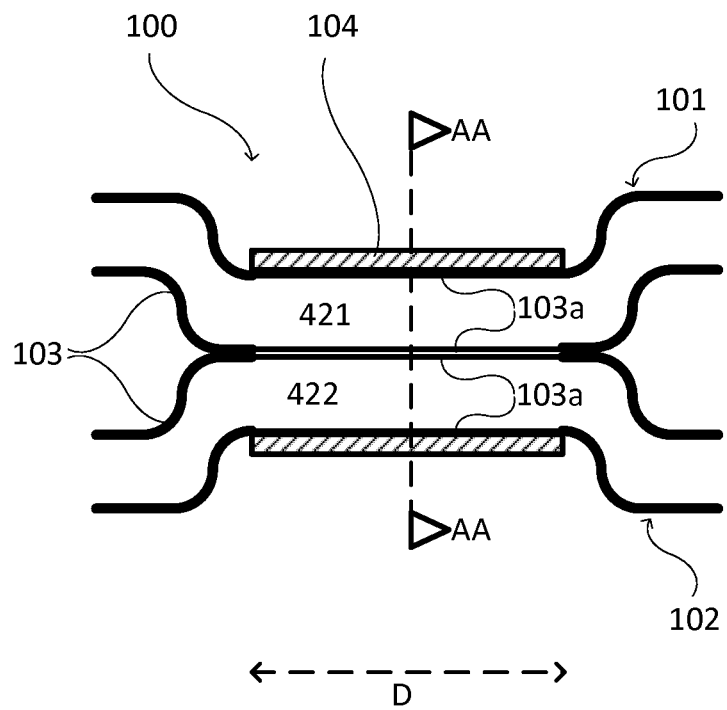
FIG. 10 represents another embodiment.
Figure 10B:
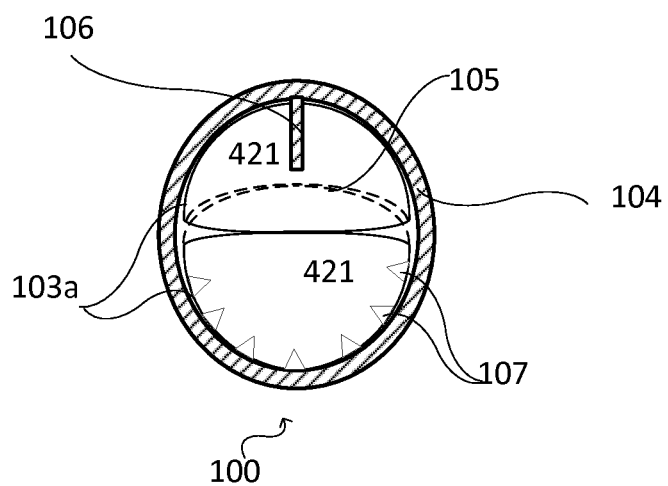

FIGS. 10a and 10b represent, respectively, longitudinal and cross-section views of another embodiment 100 of the pressure oscillation damper. Secondary volumes 421 and 422 are formed inside the tubes 101, 102 which are used to connect the pumps (not shown) to the milk expression units (not shown). The walls 103 of the tubes 101, 102 are made of a generally flexible material. However, over a length segment D of the tubes 101, 102, the walls 103a are sufficiently flexible so as to be able to expand under effects of the pressure changes within the tube. In contrast, the remaining parts of the tubes 101, 102 have walls having their usual characteristics in that they are not significantly deformed by the pressure changes within. An outer wall 104 is arranged, somewhat like a clamp, around the tubes 101, 102 along the length segment D so as to hold the tubes 101, 102 together in what could be called a bundle. It is also advantageous to have the other ends of the tubes connectable to whatever they will be used with because this makes them easier to use.

This arrangement has the advantage that the inside of the tubes 101, 102 and the secondary volumes can be in one piece and so having no discontinuities. Since discontinuities can give rise to hygiene issues, they require more rigorous cleaning so limiting their number is desirable. Here the pressure oscillation damper 40 is completed by putting the tube together and clamping the outer wall 104 around them at the appropriate point. This assembly is simpler than attaching a number of tubes to connectors.

A possible way of making the walls of the tubes 101, 102 flexible enough to expand under the pressure changes over a segment is to make the walls thinner over that length. The relative thicknesses of the segment designed to expand and remaining non-expanding parts will be a function of the characteristics of material chosen. For breast pumps, a common choice for the tube walls could be silicone rubber which has the advantage of satisfying certain hygiene requirements and being easy to mold.

Simply varying the thickness of the tube allows the manufacturing of the tube be simplified.

FIG. 10b shows a cross-section view of the embodiment of FIG. 10a along the plane AA. The outer wall 104 and tubes 101, 102 are preferably dimensioned so as to push the tubes 101, 102 together so that the parts of their walls 103a in contact are somewhat flattened, as shown. Under the action of the pressure difference between the two tubes, one tube will expand and the compress the other so that their walls 103a will adopt a position like that shown by the dotted line 105. This has the same effect as the flexible member 47 of the previous embodiments.

In the upper tube 101 is shown an embodiment of restraining member. A protuberance 106 from the outer wall 104 is arranged to project into the tube 101 and limit the expansion of the lower tube 102. It is constructed to be sufficiently stiff so as not to bend itself. It may be advantageous to arrange it as a ridge running longitudinally, though a post-like shape may be sufficient.

In the lower tube 102 is shown another embodiment of a restraining member. The outer part of the wall 103a of the tube 102 has longitudinal ridges 107 arranged inside it and projecting inwards. These are dimensioned and spaced to as to prevent complete blocking of tube 102 under the action of the expansion of tube 101 and keep tube 102 open to the required degree. Preferably, they are formed from the same material as the wall 103 of the tube 102. Also preferably, they are formed from the wall 103 as thickened portions. This arrangement further helps with the hygiene requirements in making it easier to clean the insides of the tubes 101, 102 and may make the molding of the tubes simpler.

It may be more convenient to use the same embodiment of the restraining member for both tubes though this is not obligatory.

The continuous nature of the interior of the tubes is preserved in the case of the above embodiments of the restraining member, especially where the restraining member is formed from the longitudinal ridges 106. This is advantageous for the cleaning and hygiene of the apparatus. The protuberance has the advantage that the molding of the tubes is simplified in that their inner surfaces remain smooth.

Figure 11A:
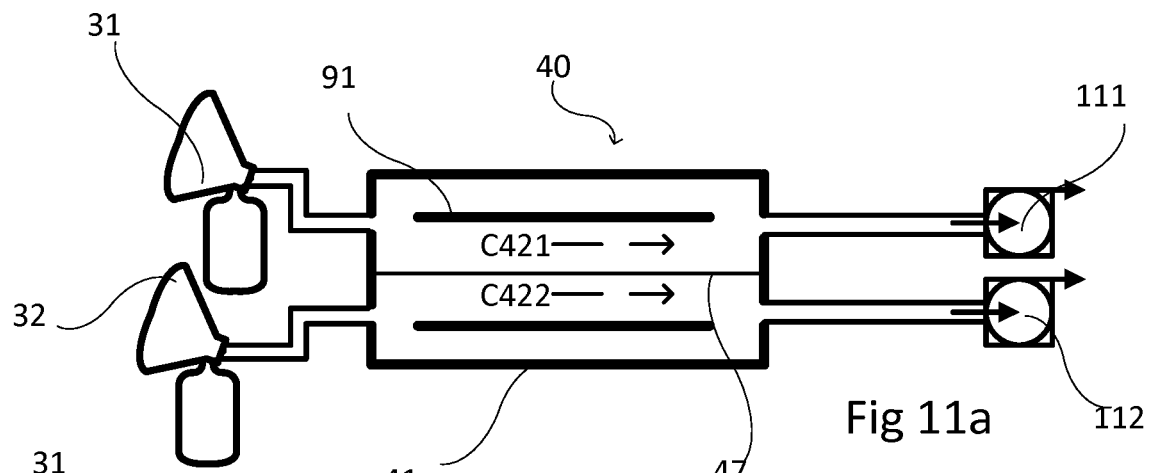
FIG. 11 represents various embodiments of a fluid extraction system.

FIGS. 11a, b and c illustrate various possible arrangements of pumps for a breast-pump system using a pressure oscillation damper 40 according to an embodiment. In FIG. 11a, two single-headed pumps 111, 112 are each coupled, via a channels C421, C422 of a pressure oscillation damper 40, to a milk expression unit 31, 32. These single-headed pumps are controlled so that their cycles are in anti-phase. This has the advantage that existing pumps may adapted and used with this system. This arrangement helps reduce the pressure oscillations felt by the user.

Figure 11B:
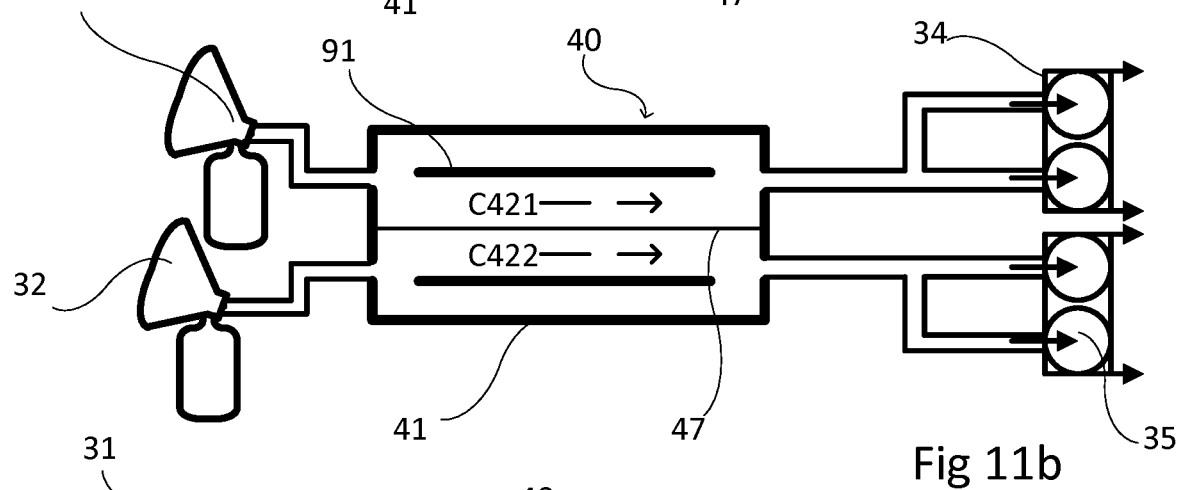

In FIG. 11b two two-headed pump 34, 35 are each coupled, via a channels C421, C422 of a pressure oscillation damper 40, to a milk expression unit 31, 32. The two-heads of pump 34 have cycles offset by 180°, giving 0° and 180° phases. Two-headed pump 35 also has cycles offset by 180° and is further offset by 90° relative to two-headed pump 34. Thus there are four inlet cycles offset by 90°. This has the advantage that each milk expression unit 31, 32 sees inlet strokes at twice the frequency that would be the case with a single headed pump which is beneficial in further reducing pressure oscillation amplitude. The pressure changes resulting from this are represented in FIG. 7b.

Figure 11C:
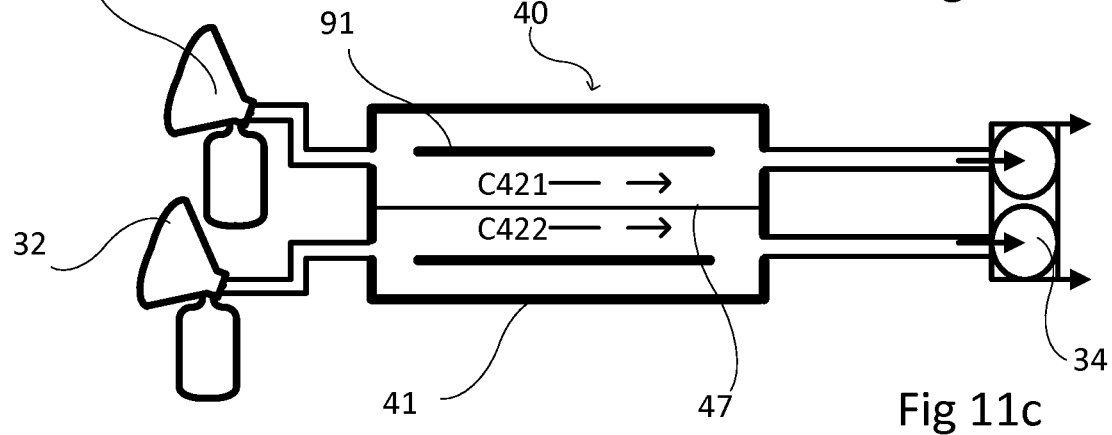

In FIG. 11c, each head of a two-headed pump 34 is coupled via a channel C421, C422 of a pressure oscillation damper 40, to a milk expression unit 31, 32. The heads of two-headed pump 34 have cycles offset by 180°. This has the advantage that two-headed pumps can be more compact that two-separate single-headed pumps.

Figure 12:
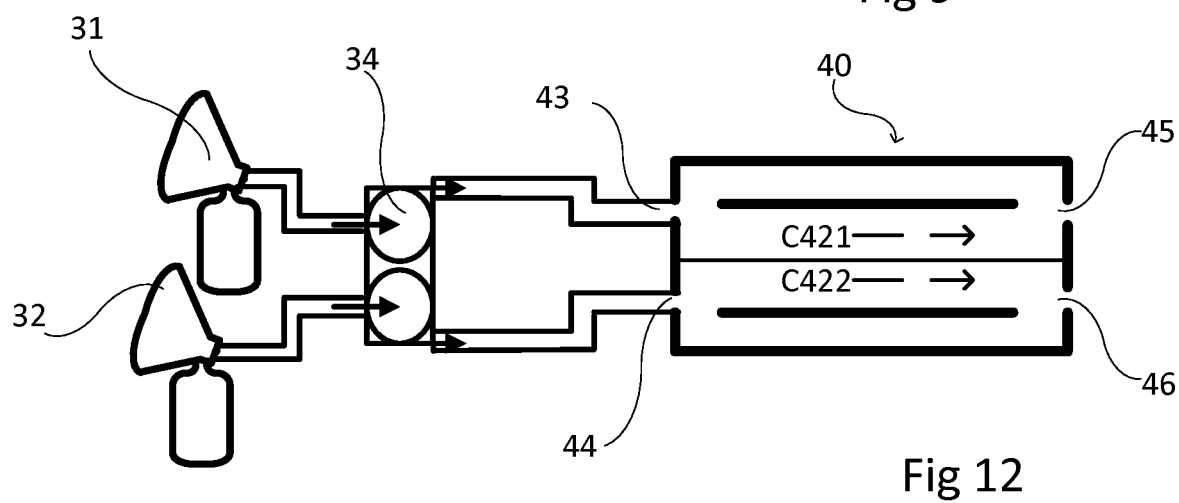
FIG. 12 represents another embodiment of a fluid extraction system.

FIG. 12 shows an example of another way of using the pressure oscillation damper. The pressure wave of the fluid being pumped out of the outlets, which in this example is air being forced out into the outside air, can be perceived as a noise. The greater is the pressure oscillation, the louder is the noise. This may, in certain situations, be undesirable. In this example of an embodiment, each of outlets of a two headed pump 34 are connected to an inlet 43, 44 of a pressure oscillation damper 40. The outlets 45, 46 are coupled to the outside air. This allows for the reduction of the pressure oscillations and so the noise of the pumping may be reduced.

The foregoing description has concerned a use as a breast pump for women desiring to express milk and the drawings show milk expression units. It should be understood that other uses are possible and these could be other fluid extraction units. For example, another possible applications is the milking of dairy cattle. Another further use could be for extracting fluid from wounds. Indeed this is another situation where the reduction of the amplitude of the pressure oscillations could be advantageous. In any situation where quieter pumping is needed, the pressure oscillation damper described herein could be useful. Still further applications are possible.

Furthermore, through silicone rubber offers some advantages of ease of molding and hygiene, in other situations, other materials could be considered. The flexible member could be made, at least in part, from one of PP foil, PE foil, PUR foil, polyester, Nylon, PVC, natural rubber, PET, polyimide, acetate film, PFTE and PEEK film. The outer wall could be made, at least in part, from one of polycarbonate, PET and styrene. There may be advantages of price or ease-of-molding offered by one or another according to the situation.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A pressure oscillation damper for a breast pump comprising:
a non-flexible outer wall enclosing a main volume;
a first inlet and a second inlet, arranged in the wall and adapted to be connected to fluid extraction units;
a first outlet and a second outlet, arranged in the wall and adapted to be connected to the breast pump, and
at least one flexible member, arranged in the main volume so as to divide the main volume into at least two secondary volumes comprising,
a first secondary volume forming a first linear horizontal channel between said first inlet and said first outlet, and
a second secondary volume forming a second linear horizontal channel between said second inlet and said second outlet,
wherein said first inlet is in the same plane as said first linear horizontal channel;
wherein said second inlet is in the same plane as said second linear horizontal channel;
wherein the at least one flexible member is configured and arranged to bend toward one of the first secondary volume and the second secondary volume having a lower pressure, and
the pressure oscillation damper further comprising:
a first restraining member arranged inside the first secondary volume, wherein the first restraining member is attached to the non-flexible outer wall and is configured and arranged to limit the bending of the at least one flexible member so as to prevent the at least one flexible member from blocking the first channel; and
a second restraining member arranged inside the second secondary volume, wherein the second restraining member is attached to the non-flexible outer wall and is configured and arranged to limit the bending of the at least one flexible member so as to prevent the at least one flexible member from blocking the second channel.

2. The pressure oscillation damper of claim 1 wherein the first and second restraining members are respective single protuberances attached to the non-flexible outer wall and arranged to project into the main volume.

3. The pressure oscillation damper of claim 1 wherein the flexible member is made of silicone rubber.

4. The pressure oscillation damper of claim 1 wherein the first restraining member is attached to the non-flexible outer wall.

5. The pressure oscillation damper of claim 1 wherein the second restraining member is attached to the non-flexible outer wall.

6. A breast pump system comprising:
a pump having at least one inlet and at least one outlet, and
a pressure oscillation damper comprising:
a non-flexible outer wall enclosing a main volume;
at least two inlets, arranged in the wall and adapted to be connected to fluid extraction units;
at least two outlets, arranged in the wall and adapted to be connected to said pump; and
at least one flexible member, arranged in the main volume so as to divide the main volume into at least two secondary volumes comprising a first secondary volume forming a first channel between a first inlet and a first outlet and a second secondary volume forming a second channel between a second inlet and a second outlet,
wherein the at least one flexible member is arranged to bend toward one of the first secondary volume and the second secondary volume having a lower pressure; and
a first restraining member arranged inside the first secondary volume, wherein the first restraining member is attached to the non-flexible outer wall and is configured and arranged to limit the bending of the at least one flexible member so as to prevent the at least one flexible member from blocking the first channel; and
a second restraining member arranged inside the second secondary volume, wherein the second restraining member is attached to the non-flexible outer wall and is configured and arranged to limit the bending of the at least one flexible member so as to prevent the at least one flexible member from blocking the second channel.

7. The fluid pumping system of claim 6 wherein the pump is a two-headed pump.

8. The fluid pumping system of claim 7 wherein both heads of the two-headed pump are coupled to one of said at least two outlets of the pressure oscillation damper.

9. The fluid pumping system of claim 6 wherein the pressure oscillation damper is coupled to the at least one inlet of the pump.

10. The fluid pumping system of claim 6 wherein the pressure oscillation damper is coupled to the at least one outlet of the pump.

11. A pressure oscillation damper for a fluid extraction system comprising:
- an outer wall enclosing a main volume;
- a first inlet arranged in the wall and adapted to be connected to a first fluid extraction unit via a first tube;
- a second inlet arranged in the wall and adapted to be connected to a second fluid extraction unit via a second tube;
- a first secondary volume formed inside the first tube;
- a second secondary volume formed inside the second tube;
- wherein a linear length segment D of the first tube seamlessly couples to a first coupling segment of the first tube at a first distal end and seamlessly couples to a second coupling segment of the first tube at a second distal end;
- wherein a linear length segment D of the second tube seamlessly couples to a first coupling segment of the second tube at a first distal end and seamlessly couples to a second coupling segment of the second tube at a second distal end; and
- wherein the linear length segment D of the first tube is thinner relative to the first and second coupling segments of the first tube; and
- wherein the linear length segment D of the second tube is thinner relative to the first and second coupling segments of the second tube, and
- wherein the thinner linear length segment D of the first and second tubes deforms to a greater degree under the effects of pressure changes relative to the first and second coupling segments of the respective first and second tubes; and
- wherein the outer wall is arranged to clamp the first and second tubes along the linear length segment D of the first and second tubes.

12. The pressure oscillation damper of claim 11, further comprising at least one protuberance, wherein the at least one protuberance is located in at least one of the first and second tubes, configured and arranged to project into one of the first and second tubes to limit the expansion of the first and second tubes under the effects of pressure changes.

13. The pressure oscillation damper of claim 12, wherein at least one protuberance is arranged as a single ridge running longitudinally along one of the first and second tubes.

14. The pressure oscillation damper of claim 12, wherein at least one protuberance is arranged as a plurality of longitudinal ridges arranged inside one of the first and second tubes, dimensioned and spaced to prevent a complete blocking of one of the first and second tubes under the act of expansion of the other of said first and second tubes.

15. The pressure oscillation damper of claim 12, wherein the first and second tubes are made of the same material as the outer wall.

16. The pressure oscillation damper of claim 12, wherein the at least one protuberance comprises a first protuberance located in the first tube and a second protuberance located in the second tube.

17. A pressure oscillation damper of claim 12, wherein the at least one protuberance is attached to an outer wall of one of the first and second tubes and arranged to project from the outer wall partially into the enclosed main volume.

18. The pressure oscillation damper of claim 12, wherein the at least one protuberance is a plurality of protuberances arranged longitudinally on the inside of the wall of the flexible tube.

* * * * *